United States Patent
Dherbassy et al.

(10) Patent No.: US 11,434,253 B2
(45) Date of Patent: Sep. 6, 2022

(54) ENANTIOPURE TERPHENYLS WITH TWO ORTHO-ATROPISOMERIC AXES

(71) Applicants: UNIVERSITE DE STRASBOURG, Strasbourg (FR); CENTRE NATIONAL DE LA RECHERCHE SCIENTIFIQUE, Paris (FR)

(72) Inventors: Quentin Dherbassy, Strasbourg (FR); Joanna Wencel-Delord, Rohrwiller (FR); Françoise Colobert, Lampertheim (FR); Gaspard Hedouin, Strasbourg (FR)

(73) Assignees: UNIVERSITE DE STRASBOURG, Strasbourg (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 125 days.

(21) Appl. No.: 16/772,284

(22) PCT Filed: Dec. 12, 2018

(86) PCT No.: PCT/EP2018/084513
§ 371 (c)(1),
(2) Date: Jun. 12, 2020

(87) PCT Pub. No.: WO2019/115597
PCT Pub. Date: Jun. 20, 2019

(65) Prior Publication Data
US 2021/0070785 A1  Mar. 11, 2021

(30) Foreign Application Priority Data

Dec. 14, 2017 (EP) .................................. 17306779

(51) Int. Cl.
| | | |
|---|---|---|
| *C07F 9/00* | (2006.01) | |
| *C07B 53/00* | (2006.01) | |
| *B01J 31/00* | (2006.01) | |
| *C07F 9/50* | (2006.01) | |
| *B01J 31/24* | (2006.01) | |

(52) U.S. Cl.
CPC ......... *C07F 9/5027* (2013.01); *B01J 31/2419* (2013.01); *B01J 31/2428* (2013.01); *C07B 53/00* (2013.01); *C07F 9/5081* (2013.01); *B01J 2231/643* (2013.01); *B01J 2231/645* (2013.01); *B01J 2531/004* (2013.01); *B01J 2531/822* (2013.01)

(58) Field of Classification Search
CPC ...... C07F 9/5027; C07F 9/5081; C07B 53/00; B01J 31/00
See application file for complete search history.

(56) References Cited

U.S. PATENT DOCUMENTS 8,318,323 B2 * 11/2012 Kato .................. H01L 51/0072
428/690

OTHER PUBLICATIONS

Database Caplus [Online] Chemical Abstracts Service, Columbus, Ohio, US; 1954, XP002780640, retrieved from STN Database Accession No. 1955:8143 (cited in ISR).
Database Caplus [Online] Chemical Abstract Service, Columbus, Ohio, US; 1961, XP002780639, retrieved from STN Database accession No. 1961:87402 (cited in ISR).
Database Caplus [Online] Chemical Abstract Service, Columbus, Ohio, US; 2009, XP002780641, retrieved from STN Database accession No. 2009:1533828 (cited in ISR).
Fogle, J., "Bis(2-fluorophenyl) Substituted PPV", Polymer Preprints, Jun. 30, 2011.
Kumar. A. et al., "Reactivity of Some Tetra Substituted Furans and Thiophenes Towards BF"3-Et"20 Catalysed Diels-Alder Reaction", Tetrahedron Letters, vol. 38, No. 6, 1997.
Li. Y. et al., "Recent advances in developing new axially chiral phosphine ligands for asymmetric catalysis," Coordination Chemistry Reviews (2007), 251, 2119-2144.
Lotter, D. et al., "Stereoselective Arene-Forming Aldol Condensation: Synthesis Configurationally Stable Oligo-1,2-naphthylenes," Angew. Chem. Int. Ed. 2016, 55, 2920-2923.
Ohkume, T. et al. In Privileged Chiral Ligands and Catalysts, Zhou, Q.-L., Ed.; Wiley-VCH Verlag GmbH & Co. KGaA: Weinheim, Germany, (2011), pp. 1-53.
Oppenheimer, J. et al., "Stereochemical Control of Both C—C and C—N Axial Chirality in the Synthesis of Chiral N,O-Biaryls," Org. Lett. 2007, 9, 3969-3972.
Veber, D. et al., "Isonicotinyloxycarbonyl, a Novel Amino Processing Group for Peptide Synthesis," J. Org. Chem., 1977, 42, 3286-3288.
Yamaguchi, K. et al., Hindered biaryls by C—H coupling: bisoxazoline-Pd catalysis leading to enantioselective C—H coupling, Chem. Sci. 2012, 3, 2165.
Yamaguchi, K. et al., "Aromatic C—H coupling with hindered arylboronic acids by Pd/Fe dual catalysts," Chem. Sci. 2013, 4, 3753.
Dherbassy et al., "Reaxys," [Online] Jan. 1, 2003, XP55831644, Database accession No. 32689103, 4 pages.
International Search Report and Written Opinion, dated Feb. 13, 2019, from corresponding PCT application No. PCT/EP2018/084513.

* cited by examiner

*Primary Examiner* — Sikarl A Witherspoon
(74) *Attorney, Agent, or Firm* — Nixon & Vanderhye

(57) ABSTRACT

Enantiopure terphenyl presenting two ortho-located chiral axes having the following structural formula (I): their process of synthesis and their use as mono or bidentate ligands for asymmetric organometallic reactions, as organocatalysts, as chiral base and as generator, with metal, of isolable chiral metallic complexes for applications in asymmetric catalysis and others.

14 Claims, 1 Drawing Sheet

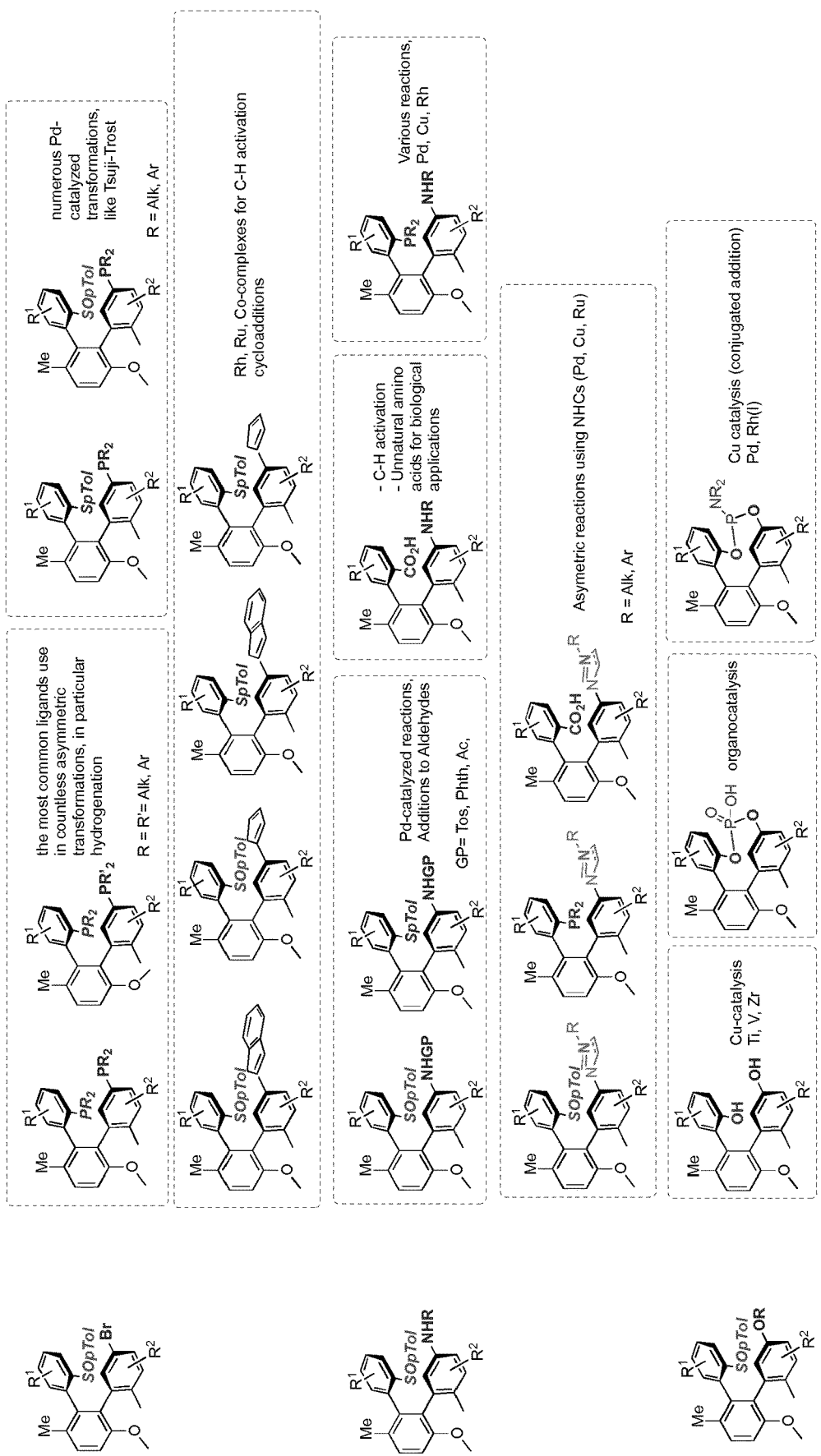

ENANTIOPURE TERPHENYLS WITH TWO ORTHO-ATROPISOMERIC AXES

BACKGROUND OF THE INVENTION

Field of the Invention

The present invention concerns enantiopure terphenyls with two ortho-atropisomeric axes, the process of synthesis thereof and their use as stereogenic scaffolds for various chiral ligands, in particular in asymmetric catalysis reactions.

Axial chirality, arising from the hindered rotation around the Ar—Ar axis of biaryl or heteroaryl-aryl compounds is an important feature of a variety of molecular scaffolds. This chirality element is the origin of unique properties of some biologically active compounds and advanced materials. But arguably the most prominent application of the atropisomeric biaryls relates to their use as stereogenic ligands in both transition metal and organocatalysis (Li, Y. et al. Coord. Chem. Rev. (2007), 251, 2119; Ohkuma, T et al. In Privileged Chiral Ligands and Catalysts, Zhou, Q.-L., Ed.; Wiley-VCH Verlag GmbH & Co. KGaA: Weinheim, Germany, (2011), pp 1-53).

Description of the Related Art

Regarding the expanding importance of asymmetric synthesis, the search for innovative atropisomeric ligands, exhibiting unusual 3D structures, is hence a continuously challenging goal.

Although both, synthesis and applications of axially chiral biaryls have been intensively studied since few decades, related optically pure scaffolds containing two contiguous atropisomeric axis are elusive. Recently, Lotter, D. et al. reported the synthesis of oligo-1,2-naphthylenes, bearing two atropocontrolled binaphthyl axis as well-defined, configurationally stable helical systems (Lotter, D. et al. *Angew. Chem. Int. Ed.* 2016, 55, 2920). In 2007, Oppenheimer, J. et al. disclosed an original method to access stereogenic molecules exhibiting both, C—C and C—N axial chiralities via asymmetric [2+2+2] cycloaddition of ynamides (Oppenheimer, J. et al., *Org. Lett.* 2007, 9, 3969).

SUMMARY OF THE INVENTION

The inventors succeeded to target the synthesis of doubly atropoisomeric terphenyls by designing an unprecedented polyfunctionalized scaffold which may be used as the precursor of original chiral ligands.

Thus one object of the present invention is an enantiopure pure terphenyl presenting two ortho-located chiral axis and having the following structural formula (I):

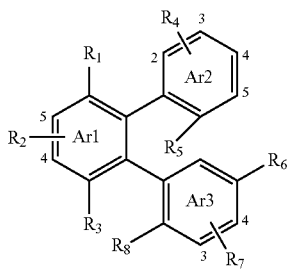

(I)

wherein $R_1$ on the phenyl ring Ar1 represents
an halogen atom, or
a substituted or unsubstituted branched or straight alkyl group, or
a substituted or unsubstituted cycloalkyl group, or
a substituted or unsubstituted branched or straight alkoxy group, or
a $CH_2F$ group, or a $CHF_2$ group or a $—CnF_{n+2}$ group avec n=1 à 10 or,
a substituted or unsubstituted aryl group or,
a $—COR_a$ or a $—COOR_a$ group with $R_a$ selected from a substituted or unsubstituted branched or straight alkyl group or a substituted or unsubstituted aryl group or
a $—NR_bR_c$ group with $R_b$ and $R_c$ independently selected from a hydrogen atom, a substituted or unsubstituted branched or straight alkyl group or a substituted or unsubstituted aryl group or forming a $NH_2$-protecting group, or
a $BR_aR_b$ group with $R_a$ and $R_b$, identical or different being as defined above or
a $—B(OR_d)(OR_e)$ group with $R_d$ and $R_e$ identical or different being selected from an hydrogen atom or a substituted or unsubstituted branched or straight alkyl group like for example a pinacolborane group,
$R_2$ in position 4 or 5 of the phenyl ring Ar1 which bears it represents
a hydrogen atom or
a halogen atom,
a substituted or unsubstituted branched or straight alkyl group or
a substituted or unsubstituted cycloalkyl group, or
a substituted or unsubstituted branched or straight alkoxy group or
a substituted or unsubstituted aryl group or
a $—COR_a$ or a $—COOR_a$ group with $R_a$ selected from a substituted or unsubstituted branched or straight alkyl group or a substituted or unsubstituted aryl group, or
a $—NR_bR_c$ group with $R_b$ and $R_c$ independently selected from a hydrogen atom, a substituted or unsubstituted branched or straight alkyl group, or a substituted or unsubstituted aryl group, or forming a $NH_2$-protecting group or
a $—BR_aR_b$ group with $R_a$ and $R_b$ identical or different being as defined above or,
a $—B(OR_d)(OR_e)$ group with $R_d$ and $R_e$ identical or different being selected from an hydrogen atom or a substituted or unsubstituted branched or straight alkyl group, like for example a pinacolborane group,
$R_3$ on the phenyl ring Ar1 represents
an halogen atom or
a substituted or unsubstituted branched or straight alkyl group or,
a substituted or unsubstituted cycloalkyl group, or
a substituted or unsubstituted branched or straight alkoxy group or
a substituted or unsubstituted aryl group or
a $—COR_a$ or a $—COOR_a$ group with $R_a$ selected from a substituted or unsubstituted branched or straight alkyl group or a substituted or unsubstituted aryl group, or
a $—NR_bR_c$ group with $R_b$ and $R_c$ independently selected from a hydrogen atom, a substituted or unsubstituted branched or straight alkyl group, or a substituted or unsubstituted aryl group, or forming a $NH_2$-protecting group,
a $—BR_aR_b$ group with $R_a$ and $R_b$ identical or different being as defined above or, a —B(OR$_d$)(OR$_e$) group with R$_d$ and R$_e$ identical or different being selected from an hydrogen atom or a substituted or unsubstituted branched or straight alkyl group, like for example a pinacolborane group, R$_4$, which may be in position 2, 3, 4 or 5 on the phenyl ring Ar2 which bears it, represents:
a hydrogen atom or
a halogen atom or
a substituted or unsubstituted branched or straight alkyl group or,
a substituted or unsubstituted cycloalkyl group, or
a CH$_2$F group, or a CHF$_2$ group or —C$_n$F$_{n+2}$ group avec n =1 à 10, or
a substituted or unsubstituted aryl group, or
a —OR$_a$, a —COR$_a$ or a —COOR$_a$ group with R$_a$ selected from a substituted or unsubstituted branched or straight alkyl group or a substituted or unsubstituted aryl group, or
a —NR$_b$R$_c$ group with R$_b$ and R$_c$ independently selected from a hydrogen atom, a substituted or unsubstituted branched or straight alkyl group, or a substituted or unsubstituted aryl group, or forming a NH$_2$-protecting group, or
a —BR$_a$R$_b$ group with R$_a$ and R$_b$ identical or different being as defined above or,
a —B(OR$_d$)(OR$_e$) group with R$_d$ and R$_e$ identical or different being selected from an hydrogen atom or a substituted or unsubstituted branched or straight alkyl group, like for example a pinacolborane group, R$_5$ on the phenyl ring Ar1 represents a coordinating group or a substituent that will be used to install a coordinating group, selected from:
an halogen atom,
an iodine atom in different oxidation state from I(I) to I(V),
an —OR$_b$ group with R$_b$ selected from a hydrogen atom, a substituted or unsubstituted branched or straight alkyl group, or a substituted or unsubstituted aryl group, or a NH$_2$-protecting group or
a —CH$_2$OR$_b$ group with R$_b$ selected from a hydrogen atom, a substituted or unsubstituted branched or straight alkyl group, or a substituted or unsubstituted aryl group, or
a —CHO group or
a —COOR$_b$ group with R$_b$ selected from a hydrogen atom, a substituted or unsubstituted branched or straight alkyl group, or a substituted or unsubstituted aryl group, or a NH$_2$-protecting group, or
a —NR$_b$R$_c$ group with R$_b$ and R$_c$ independently selected from a hydrogen atom, a substituted or unsubstituted branched or straight alkyl group, or a substituted or unsubstituted aryl group, or a NH$_2$-protecting group,
a —SOR$_a$ group or a —SR$_a$ group or a —SO$_2$R$_a$ with R$_a$ selected from a substituted or unsubstituted branched or straight alkyl group or a substituted or unsubstituted aryl group, or
a —PR$_a$n$_d$ or a —P(O)R$_a$n$_d$ with R$_a$ and R$_d$ independently selected from a substituted or unsubstituted branched or straight alkyl group or a substituted or unsubstituted aryl group, or
a —C=NR$_b$ with R$_b$ as defined above or
a substituted or unsubstituted oxazoline group or
a substituted or unsubstituted indenyl group or
a substituted or unsubstituted cyclopentadienyl group, R$_6$ on the phenyl ring Ar3 is a coordinating group either represents
a hydrogen atom or
an halogen atom,
an iodine atom in different oxidation state from I(I) to I(V), or
an —OH group
a substituted or unsubstituted branched or straight alkyl group or
a substituted or unsubstituted cycloalkyl group, or
a substituted or unsubstituted aryl group or
a —SOR$_a$ group or a —SR$_a$ group or a —SO$_2$R$_a$ with R$_a$ selected from a substituted or unsubstituted branched or straight alkyl group or a substituted or unsubstituted aryl group, or
a —OR$_a$, a —COR$_a$ or a —COOR$_a$ group with R$_a$ selected from a substituted or unsubstituted branched or straight alkyl group or a substituted or unsubstituted aryl group, or
a —NR$_b$R$_c$ group with R$_b$ and R$_c$ independently selected from a hydrogen atom, a substituted or unsubstituted branched or straight alkyl group, or a substituted or unsubstituted aryl group, or forming a NH$_2$-protecting group or,
a —BR$_a$R$_b$ group with R$_a$ and R$_b$ identical or different being as defined above or,
a —B(OR$_d$)(OR$_e$) group with R$_d$ and R$_e$ identical or different being selected from an hydrogen atom or a substituted or unsubstituted branched or straight alkyl group, like for example a pinacolborane group,
a —PR$_a$n$_d$ or a —P(O)R$_a$n$_d$ with R$_a$ and R$_d$ independently selected from a substituted or unsubstituted branched or straight alkyl group or a substituted or unsubstituted aryl group, or
a substituted or unsubstituted or oxazoline group
a substituted or unsubstituted indenyl group or
a substituted or unsubstituted cyclopentadienyl group
or may form with R$_5$
a bridged phosphoric acid or ester or phosphinate represented by formula

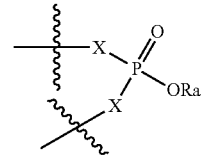

with X being a carbon or an oxygen atom and Ra selected from an hydrogen atom or a substituted or unsubstituted branched or straight alkyl group; or
a bridged phosphoramidite or phosphoramine represented by formula

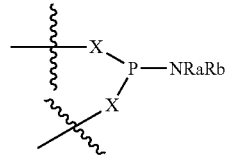

with X being a carbon or an oxygen atom and Ra and Rb selected from a substituted or unsubstituted branched or straight alkyl group or a substituted or unsubstituted aryl group, $R_7$ which may be in position 3 or 4 on the phenyl ring Ar3 which bears it represents:
- a hydrogen atom or
- a halogen atom or
- a substituted or unsubstituted branched or straight alkyl group or,
- a substituted or unsubstituted branched or straight alkoxy group
- a substituted or unsubstituted cycloalkyl group, or
- a $CH_2F$ group, or a $CHF_2$ group or —$CnF_{n+2}$ group avec n=1 à 10, or
- a substituted or unsubstituted aryl group, or
- a —$OR_a$, a —$COR_a$ or a —$COOR_a$ group with $R_a$ selected from a substituted or unsubstituted branched or straight alkyl group or a substituted or unsubstituted aryl group, or
- a —$NR_bR_c$ group with $R_b$ and $R_c$ independently selected from a hydrogen atom, a substituted or unsubstituted branched or straight alkyl group, or a substituted or unsubstituted aryl group, or forming a $NH_2$-protecting group, or
- a —$BR_aR_b$ group with $R_a$ and $R_b$ identical or different being as defined above or,
- a —$B(OR_d)(OR_e)$ group with $R_d$ and $R_e$ identical or different being selected from an hydrogen atom or a substituted or unsubstituted branched or straight alkyl group, like for example a pinacolborane group, $R_8$ on the phenyl ring Ar3 represents
- an halogen atom or
- a substituted or unsubstituted branched or straight alkyl group, or a substituted or unsubstituted branched or straight alkoxy group or
- a —$OR_a$ group with $R_a$ selected from a substituted or unsubstituted branched or straight alkyl group or a substituted or unsubstituted aryl group, or
- a substituted or unsubstituted aryl group or
- a —$COR_a$ or a —$COOR_a$ group with $R_a$ selected from a substituted or unsubstituted branched or straight alkyl group or a substituted or unsubstituted aryl group, or
- a —$NR_bR_c$ group with $R_b$ and $R_c$ independently selected from a hydrogen atom, a substituted or unsubstituted branched or straight alkyl group, or a substituted or unsubstituted aryl group, or a forming $NH_2$-protecting group, or
- a —$BR_aR_b$ group with $R_a$ and $R_b$ identical or different being as defined above or,
- a —$B(OR_d)(OR_e)$ group with $R_d$ and $R_e$ identical or different being selected from an hydrogen atom or a substituted or unsubstituted branched or straight alkyl group, like for example a pinacolborane group.

The substituents are selected as follows:
$R_1$, $R_3$ and $R_8$ confer atropostability to the molecule,
$R_5$ is the first coordination site and $R_6$ is a second coordination site,
$R_2$, $R_4$ and $R_7$ are substituents able to tune electronic and steric properties of the molecule.

According to the invention, compounds of formula (I) may also exist as salts which belong to the invention. Said salts may be prepared according to process known the art.

Compounds of formula (I) possess two chiral axes which are totally controlled and are enantiopure compounds, i.e. compound existing only as one enantiomer.

The expression enantiopure compound is understood to mean a chiral compound mainly consisting of one enantiomer.

The substituents on the compounds of formula (I) will be described hereunder. An halogen atom includes a fluorine atom, a chlorine atom, a bromine atom and an iodine atom.

A substituted or unsubstituted branched or straight alkyl group is a $C_1$-$C_{10}$, preferably $C_1$-$C_6$, most preferably $C_1$-$C_5$ alkyl chain and includes for example a methyl group, an ethyl group, a n-propyl group, an isopropyl group, a n-butyl group and a tert-butyl group, a 2-hydroxyethyl group, a 2-hydroxypropyl group, a 3-hydroxypropyl group, a 2-hydroxybutyl group, a 3-hydroxybutyl group, a 4-hydroxybutyl group, a 2,3-dihydroxypropyl group, a 3,4-dihydroxybutyl group, a pentyl group, a neopentyl group, an hexyl group an heptyl group, an octyl group, a nonyl group, a decyl group and the like. These groups may be substituted by one or several substituents selected from unsubstituted branched straight($C_1$-$C_{10}$)alkyl group and unsubstituted branched or straight-($C_1$-$C_{10}$)alkoxy group. A substituted or unsubstituted cycloalkyl group is a $C_3$-$C_{10}$, preferably $C_3$-$C_6$, most preferably $C_5$-$C_7$ cyloalkyl chain including a cyclopropyl group, a cyclobutyl group, a cyclopentyl group, a cyclohexyl group, a cycloheptyl group, a cyclooctyl group, a cyclononyl group and a cyclodecyl group and the like.

A substituted or unsubstituted branched or straight alkoxy group is a $C_1$-$C_{10}$, preferably $C_1$-$C_6$, most preferably $C_1$-$C_5$ acyl chain and includes for example a methoxy group, an ethoxy group, a n-propoxy group, an isopropoxy group, a n-butoxy group, a tert-butoxy group, a pentoxy group, a and the like. These groups may be substituted by one or several substituent selected from unsubstituted branched straight-($C_1$-$C_{10}$)alkyl group and unsubstituted branched or straight-($C_1$-$C_{10}$)alkoxy group.

A substituted or unsubstituted aryl group includes a phenyl group or a naphtyl group or a heteroaromatic group, each of them being optionally substituted by one or several substituent selected from unsubstituted branched straight-($C_1$-$C_{10}$)alkyl group and unsubstituted branched or straight-($C_1$-$C_{10}$)alkoxy group.

A $NH_2$-protecting group is known per se as chemical functional groups that can be selectively appended to and removed from amine groups, present in a chemical compound to render such functionality inert to chemical reaction conditions to which the compound is exposed. See, e.g., Greene and Wuts, Protective Groups in Organic Synthesis, 2d edition, John Wiley & Sons, New York, 1991. Numerous amine protecting groups are known in the art, including the acetyl, phtalimide (Phth), tolyl (Tol), tosyl (SO2to1) benzyl (Bn), benzyloxycarbonyl (CBz), chlorobenzyloxycarbonyl, t-butyloxycarbonyl (Boc), fluorenylmethoxycarbonyl (Fmoc), isonicotinyloxycarbonyl (i-Noc) groups. (see, e.g., Veber and Hirschmann, et al., J. Org. Chem., 1977, 42, 3286 and Atherton, et al., The Peptides, Gross and Meienhofer, Eds, Academic Press; New York, 1983; Vol. 9 pp. 1-38).

In an advantageous embodiment of the invention, the terphenyls of the invention are those of formula (I) wherein
$R_1$ represents
- an halogen atom,
- a substituted or unsubstituted branched or straight alkyl group or
- a substituted or unsubstituted branched or straight alkoxy group or
- a $CF_3$ group, $R_2$ represents
- a hydrogen atom or
- a substituted or unsubstituted branched or straight alkyl group, or
- a substituted or unsubstituted branched or straight alkoxy group $R_3$ represents a substituted or unsubstituted branched or straight alkyl group or a substituted or unsubstituted branched or straight alkoxy group, $R_4$ represents a hydrogen atom or a halogen atom or a substituted or unsubstituted branched or straight alkoxy group, or a substituted or unsubstituted branched or straight alkyl group or a aryl group or a $CH_2F$ group, or a $CHF_2$ group or —$CnF_{n+2}$ group avec n=1 à 10, or $R_5$ represents a $SOR_a$ group with $R_a$ selected from a substituted or unsubstituted branched or straight($C_1$-$C_4$) alkyl group or a substituted or unsubstituted aryl group, or a OH group, or —$PR_an_d$ or a —$P(O)R_an_d$ with $R_a$ and $R_d$ independently selected from a substituted or unsubstituted branched or straight alkyl group or a substituted or unsubstituted aryl group, $R_6$ represents a hydrogen atom, a halogen atom or a substituted or unsubstituted branched or straight-($C_1$-$C_4$) alkyl group or a substituted or unsubstituted branched or straight-($C_1$-$C_4$) alkoxy group or —$PR_an_d$ or a —$P(O)R_an_d$ with $R_a$ and $R_d$ independently selected from a substituted or unsubstituted branched or straight alkyl group or a substituted or unsubstituted aryl group, or a —$NR_bR_c$ group with $R_b$ and $R_c$ independently selected from a hydrogen atom, a substituted or unsubstituted branched or straight alkyl group, or a substituted or unsubstituted aryl group, or a $NH_2$-protecting group, $R_7$ represents a hydrogen atom, a substituted or unsubstituted branched or straight-($C_1$-$C_4$) alkyl group or a substituted or unsubstituted branched or straight-($C_1$-$C_4$) alkoxy group or a $CF_3$ group, $R_8$ represents a hydrogen atom, a halogen atom, a substituted or unsubstituted branched or straight-($C_1$-$C_4$) alkyl group or a substituted or unsubstituted branched or straight-($C_1$-$C_4$) alkoxy group or a $CF_3$ group In an advantageous embodiment of the invention, the terphenyls of the invention are those given in the examples and in the figure.

Aiming the potential applications of compounds of formula (I)

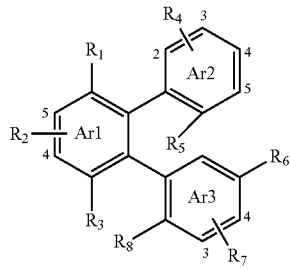

in asymmetric catalysis, several key points need to be considered.

The ortho-geometry between the phenyl (Ar2) bearing $R_4$ and $R_5$ and the phenyl (Ar3) bearing $R_6$, $R_7$ and $R_8$ is crucial, as it guarantees proximity in space between these two external aromatic rings. Such architecture 1) gives a possibility to install coordinating moieties on each aromatic ring and 2) ensures a mutually dependent stereogenic environment (for example position and steric hindrance of Ar2 will directly impact the positioning of Ar3). Besides, the substitution of the three aromatics is of key importance: 1) to allow coordination of a metal by a directing group, ideally convertible into various coordinating motifs; 2) to warrant the atropostability of both chiral axis 3) to modify the electronic and steric properties of the scaffolds 4) to bring a secondary coordination site. Hence designed molecular structures seem perfectly adapted to accommodate a metal atom (organometallic catalysis) or an organic molecule (organocatalysis) in a "sea shell"-fashion.

The asymmetric synthesis of compounds of formula (I) presents a veritable synthetic defy. Targeting their modular and straightforward, step- and waste-economic preparation, a C—H activation route, implying a direct arylation of a biaryl precursor seems particularly appealing. To reach this goal, three fundamental challenges need to be addressed. Firstly, the direct Ar—Ar bond formation between two sterically demanding coupling partners must be performed, whereas direct arylations using ortho-substituted iodoarenes are recognized as highly challenging and ortho-metallation at sterically congested positions is extremely rare. Secondly, as the stereoselective transformation is targeted, the inherent antagonism between efficiency and atroposelectivity has to be overcome. The third fundamental difficulty concerns the perfect stereocontrol of two asymmetric events during one C—H activation reaction: 1) atroposelective introduction of an aryl substituent on a configurationally unstable biaryls precursor via Kinetic Dynamic Resolution (control of the Ar1-Ar2 bond) and 2) direct stereoselective Ar1-Ar3 bond formation. Although several protocols concerning atroposelective C—H functionalization of biaryls have been reported in the literature, these examples are limited to oxidative Heck reaction, direct C—O and C—I couplings while introduction of an Ar substituent remains unexplored. More challengingly, the atroposelective Ar—H/Ar—X coupling, implying reaction between two sterically demanding partners is virtually unparalleled. The unique example disclosed in the literature concerns direct bond formation between hindered thiophene and naphthylboronic acid (Yamaguchi, K et al. Chem. Sci. 2012, 3, 2165; Yamaguchi, K.; et al. Chem. Sci. 2013, 4, 3753) whereas a directed transformation implying two aromatics remains unprecedented.

The inventors have worked out an unprecedented process for the synthesis of compounds of formula (I).

Thus another object of the invention is a process for preparing the compounds of formula (I), said process comprising the step of:

reacting a compound of formula (1)

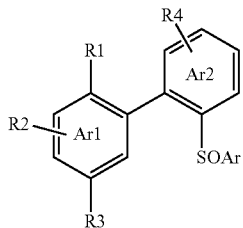
(1)

wherein $R_1$, $R_2$, $R_3$ and $R_4$ are as defined above and Ar is selected from substituted or unsubstituted aryl groups, with a compound of formula (2)

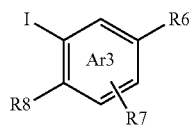
(2)

with $R_6$, $R_7$ and $R_8$ as defined above, in presence of a silver salt comprising a mixture of $Ag_2CO_3$ and AgTFA, a N-heterocyclic carbene precursor like for example 1,3-Bis(2,6-diisopropylphenyl) imidazolium chloride (iPrHCl), a palladium catalyst like $Pd(TFA)_2$ and a molecular sieve of 3 Å to 5 Å, preferably of 4 Å in a solvent selected from the flurorinated alcool or fluorinated ethers, like 1,1,1,3,3, 3-Hexafluoro-2-propanol (Hexafluoroisopropanol or HFIP) at a temperature comprised between 40 and 120° C., advantageously between 75 and 85° C. during 2 to 24 hours, preferably 2 to 10 hours to obtain a compound of formula (Ia)

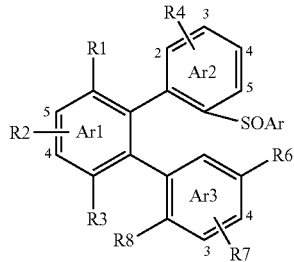
(Ia)

wherein $R_1$, $R_2$, $R_3$, $R_4$, $R_6$, $R_7$ and $R_8$ are as defined above and Ar is selected from substituted or unsubstituted aryl groups, functionalizing the —SOAr group in order to obtain a compound of formula (I)

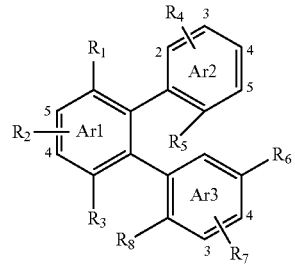
(I)

wherein $R_1$, $R_2$, $R_3$, $R_4$, $R_6$, $R_7$ and $R_8$ are as defined above and $R_5$ is as defined above and is not —SOAr.

Compounds of formula (1) are prepared by processes known from the one skilled in the art or described in the literature.

In an advantageous embodiment of the invention compounds of formula (1) are prepared by reacting a boronic acid of formula (3)

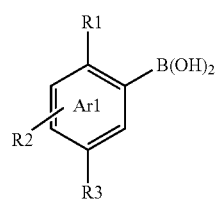
(3)

wherein $R_1$, $R_2$ and $R_3$ are as defined above with a compound of formula (4)

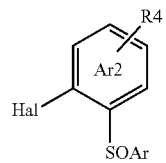
(4)

wherein $R_4$ and SOAr are as defined above and Hal represents a halogen atom selected from bromide and iodide.

Compounds of formula (3) are commercially available or may be prepared by processes known from the one skilled in the art or described in the literature.

Compounds of formula (4) are prepared by processes known from the one skilled in the art or described in the literature.

The enantiopure compounds of formula (1)

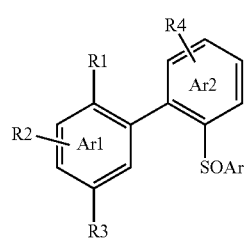
(1)

wherein $R_1$, $R_2$, and $R_4$ are as defined above, $R_3$ is as defined above but is not hydrogen and Ar is selected from substituted or unsubstituted aryl groups,
are new and are also part of the invention. They are useful as intermediary compounds in the synthesis of compounds of formula (I).

The compounds of formula (I) according to the invention are chiral and enantiopure, with a unique stereogenic architecture. They can therefore be used as mono or bidentate ligands for asymmetric organometallic reactions, as organocatalysts, or as chiral hypervalent iodine as chiral base and can generate with metal, isolable chiral metallic complexes for applications in asymmetric catalysis and others.

Thus another object of the invention are asymmetric organometallic reactions comprising the step of using a compound of formula (I) as mono or bidentate ligands.

The ligand according to the invention are also useful for asymmetric hydrogenation, in particular asymmetric hydrogenation of imines for which the known catalysts do not give good results.

BRIEF DESCRIPTION OF THE DRAWING

The sole drawing figure illustrates the terphenyls disclosed.

DESCRIPTION OF THE PREFERRED EMBODIMENTS

The following examples 1 to 7 illustrate the invention.
General Experimental Part
Unless otherwise noted, all reagents were purchased from commercial suppliers (Sigma-Aldrich, Acros, Alfa Aesar, Fluorochem) and were used without further purification.

Anhydrous solvents term denotes solvents dried over molecular Sieves (to the fresh commercial solvent bottle were added 3 or 4 angstrom MS in beads form, followed by static drying for at least 48 hours before use), kept under Argon and handle using the standard Schlenk techniques:
- Tetrahydrofuran (THF) was dried using 10% (m/v) 3 or 4 Å MS
- Diethylether was dried using 10% (m/v) 3 or 4 Å MS
- Dichloromethane and Toluene were purchased from Aldrich (Sure/Seal packaging, kept over 3 Å molecular sieves).
- 1,1,1,3,3,3-hexafluoroisopropanol (HFIP) was purchased from Fluorochem and dried sequentially 2 times over 3 Å MS (each time 20% (m/v), static drying for 72 hours).
- Molecular sieves were activated by heating at ~300° C. under vacuum overnight.

Organolithium and organomagnesium reagents were titrated before use.

Flash chromatography refers to column chromatography using silica gel (Merck 60, 40-63 μm size), driven by pressurized air.

Thin layer chromatography (TLC): was carried out using Merck Kieselgel 60 $F_{254}$ silica gel plates.

NMR: recorded on Brücker Avance 500, 400 or 300, the FID was treated with MestRec Nova, TopSpin. The chemical shift (δ) is given relative to the residual signal of the solvent ($CHCl_3$: δ ($^1H$)=7.26 ppm; δ ($^{13}C$)=77.16 ppm. $CD_3CN$: δ ($^1H$)=1.94 ppm; δ ($^{13}C$)=1.32 ppm), or relative to an external standard ($CFCl_3$: δ ($^{19}F$)=0 ppm; $H_3PO_4$ (85%)=0 ppm). Broad=Br, singulet=s, doublet=d, triplet=t, quadruplet=q, multiplet=m.

Specific description of signals: 7.06-7.03 (AA'BB', 2H) refers to an AA'BB' spin system, where the AA' multiplet part covers from 7.06 to 7.03 ppm and integrates for 2 protons.

Mixture of atropisomer on the NMR time scale: compounds that are not considered atropisomeric, in the sense that each atropisomer can be isolated, might exhibit atropisomeric feature on the NMR time scale. Indeed, if two atropodiastereoisomers are possible by symmetry consideration, each can give well-defined and resolved spectra. This is dependent on the rate of interconversion between the two atropodiastereoisomers, the chemical shift difference between the signals, and the temperature.

HRMS measurements were performed by Service de Spectrométrie de Masse de L'institut de Chimie at the University of Strasbourg.

Elemental Analysis measurements were performed by the Analytical, Physical Measurements and Optical Spectroscopy Service of the University of Strasbourg.

EXAMPLE 1: BIARYL PRECURSORS 1.1. (−)-Menthyl-(S)-p-toluenesulfinate

Said Compound is Commercially Available 1.2. (S)-1-bromo-2-(p-tolylsulfinyl)benzene

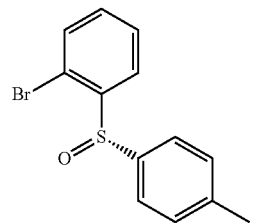

(S)-1-bromo-2-(p-tolylsulfinyl)benzene
Chemical Formula: $C_{13}H_{11}BrOS$
Molecular Weight; 295,1940

2-bromoiodobenzene (1 eq., 20 g, 9.08 mL, 70.7 mmol) was dissolved in THF (40 mL) and cooled down to 0° C. A solution of i-PrMgCl (35.35 mL, 70.7 mmol, 2M in THF) was added dropwise and the resulting mixture stirred for 1 hour at 0° C. It was then cannulated on a solution of (−)-(1R,2S,5R)-menthyl (S)-p-toluenesulfinate (1 equiv, 0.25M in anhydrous THF) (1 eq., 20.8 g, 70.7 mmol) in THF (200 mL) at −40° C. The reaction was then allowed to come back to 0° C. over 2-3 hours when it was diluted with $Et_2O$ and quenched by a sat.sol. of $NH_4Cl$. The phases were separated, the aqueous phase extracted once with $Et_2O$ and the combined organic phases dried over $Na_2SO_4$. The solvent was removed under reduced pressure and the crude oily product was quickly dissolved in 100 mL of $Et_2O$ and allowed to crystallize at 4-6° C. for several hours. The crystals were collected and washed with n-pentane. The mother liquor was concentrated and again dissolved $Et_2O$ to afford a second batch of equal purity ($^1H$ NMR), yielding a total of (S)-1-bromo-4-methyl-2-(p-tolylsulfinyl)benzene as colorless crystals (18.06 g, 61.2 mmol, 86.5%).

$^1H$-NMR (400 MHz, $CDCl_3$): δ=8.06 (dd, J=7.8, 1.6 Hz, 1 H), 7.63 (d, J=8.2 Hz, 2 H), 7.56 (ddd, J=7.8, 7.4, 1.0 Hz, 1 H), 7.51 (dd, J=8.0, 1.0 Hz, 1 H), 7.32 (ddd, J=8.0, 7.4, 1.6 Hz, 1 H), 7.24 (d, J=8.2 Hz, 2 H), 2.36 (s, 3 H) ppm.

$^{13}$C-NMR (101 MHz, CDCl$_3$): δ=145.1, 142.1, 141.3, 133.1, 132.2, 130.0 (2 $C_{pTol}$), 128.5, 126.4 (2 $C_{pTol}$), 126.3, 120.0, 21.5 ppm.

R$_f$ (EtOAc/c-Hex 1:2)=0.42.

[α]$_D^{20}$=−161 (c=1, CHCl$_3$).

Chiral HPLC e.r. >99% [OD-H column, n-Hex/i-PrOH 80:20, 0.5 mL/min, (R) r$_t$=13.49 min, (S) r$_t$=16.01 min].

1.3. 2-bromo-4-methoxy-1-methylbenzene

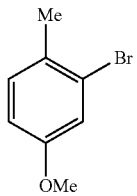

2-bromo-4-methoxy-1-methylbenzene
Chemical Formula: C$_8$H$_9$BrO
Molecular Weight; 201,0630

3-bromo-4-methylphenol (1 eq., 5 g, 26.7 mmol) was dissolved in DCM (200 mL) along with triethylbenzylammonium chloride (5%, 0.304 g, 1.34 mmol) and dimethyl sulfate (1.2 eq., 4.05 g, 3.04 mL, 32.1 mmol). Then, under vigorous stirring, NaOH (19 M, 2.5 eq.,3.5 mL) was added dopwise at room temperature. The reaction mixture became orange and turbid, then after 2 hours it regained its original greenish color. Water was then added (100 mL), and the mixture was stirred for 1 more hour. Then an ammonium hydroxide solution (10 mL) was added to quench the excess dimethyl sulfate, and the mixture was stirred for 1 more hour. The phases were then separated and the organic phase was washed with a 1M NaOH solution (1M), a sat. sol. of NaHCO$_3$, and with a 1M HCl solution (2 times). The product 2-bromo-4-methoxy-1-methylbenzene (5.02 g, 25 mmol, 93%), isolated as an orange oil, is pure enough to be used in the next step (the crude $^1$H NMR is given in the SI).

$^1$H-NMR (CDCl$_3$, 400 MHz): δ=7.12 (d, J=8.4 Hz, 1H), 7.10 (d, J=2.6 Hz, 1H), 6.77 (dd, J=8.4, 2.7 Hz, 1H), 3.77 (s, 3H), 2.33 (s, 3H) ppm. Spectral data matched the literature.

1.4. (5-methoxy-2-methylphenyl)boronic acid

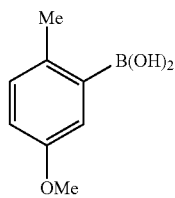

(5-methoxy-2-methylphenyl)boronic acid
Chemical Formula: C$_8$H$_{11}$BO$_3$
Molecular Weight; 165,9830

Mg turnings (3 eq., 3.97 g, 163 mmol) were loaded in a two-necked flask, followed by THF (10 mL) at room temperature. The magnesium was activated by dibromoethane (0.0531 eq., 0.543 g, 0.25 mL, 2.89 mmol), and then under stirring a solution of 2-bromo-4-methoxy-1-methylbenzene (1 eq., 11 g, 54.5 mmol) in THF (40 mL) was added dropwise at a rate sufficient to obtain a refluxing solution. After the addition, the light grey solution was stirred for a further 1 h. at 50° C. Then, after cooling to room temperature, the reaction mixture was diluted with THF (50 mL), and cooled down to 0° C. Then, under vigorous stirring, neat B(OMe)$_3$ (3.5 eq., 19.8 g, 21.6 mL, 190 mmol) was quickly added in one portion, which caused a white precipitate to appear. After 15 min. of stirring at 0° C., the cooling bath was removed and the reaction mixture was stirred for 1 h. at room temperature. The reaction was then quenched by a 1M HCl solution, and stirred for 1h., diluted with Et$_2$O, and the phases were separated. The aqueous phase was extracted with an Et$_2$O/THF mixture (1:1, v/v), and the combined organic phases were dried over Na$_2$SO$_4$. The volatile were removed under reduced pressure and the crude off-white solid thus obtained was triturated with n-pentane under sonication. The crude product is then recrystallized from MeCN (reflux to room temperature to 4-6° C. The titled compound (5-methoxy-2-methylphenyl)boronic acid (7.33 g, 44.2 mmol, 81%) was obtained as a white solid. The title compound as a low solubility in most water-free organic solvents except for THF.

$^1$H NMR (NCCD$_3$, 400 MHz): δ=7.07 (d, J=8.3 Hz, 1H), 7.04 (d, J=2.8 Hz, 1H), 6.82 (dd, J=8.3, 2.9 Hz, 1H), 6.14 (s, 2H), 4.87 (s, 2H signal corresponding to the hydrated boronic acid, due the water-contaminated NCCD$_3$), 3.75 (s, 3H), 2.36 (s, 3H) ppm.

EXAMPLE 2: DI-ORTHO-SUBSTITUTED BIPHENYLS 2. (S)-5-methoxy-2-methyl-2'-(p-tolylsulfinyl)-1,1'-biphenyl

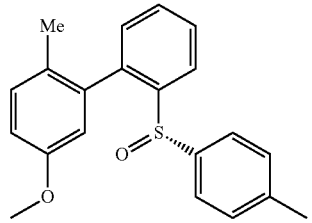

(S)-5-methoxy-2-methyl-2'-(p-tolysulfinyl)-1,1'-biphenyl
Chemical Formula: C$_{21}$H$_{20}$O$_2$S
Molecular Weight: 336,4490

(S)-1-bromo-2-(p-tolylsulfinyl)benzene (1 eq., 3.87 g, 13.1 mmol), Pd(OAc)$_2$ (2.5 mol %, 0.0735 g, 0.327 mmol), TBAB (0.999 eq., 4.22 g, 13.1 mmol) and Na$_2$CO$_3$ (3 eq., 4.16 g, 39.3 mmol) were loaded under air in a round-bottom flask. EtOH (8 mL) was then added under gentle stirring in order to dissolve the organic reagents and to obtain a thick paste. The resulting heterogeneous solution was heated at 100° C., water (75 mL) was added and the reaction mixture was stirred vigorously for 3 hours at 100° C. After having cooled down to room temperature, the reaction was diluted with Et$_2$O and stirred for 10-15 min. It was then transferred to a separating funnel; diluted with more Et$_2$O and a 1M NaOH solution, and the phases were separated. The organic phase was dried over Na$_2$SO$_4$ and the solvent removed under reduced pressure. The crude product was then purified by flash chromatography. The crude product was purified quickly by careful filtration on silica gel, followed by recrystallization from a 95:5 heptane/toluene mixture (reflux to room temperature then to 4-6° C.). The solution is seeded while hot and left undisturbed, yielding (S)-5-methoxy-2-methyl-2'-(p-tolylsulfinyl)-1,1'-biphenyl (3.8 g, 11.3 mmol, 86%) as white crystals. The seed crystals are obtained by careful recrystallization of the pure product after column chromatography from a 95:5 heptane/toluene mixture (reflux to room temperature then to 4-6° C.). Mixture of two atropisomer (1:1) on the NMR time scale.

$^1$H-NMR (CDCl$_3$, 400 MHz): 8.25 (dd, J=7.9, 1.2 Hz, 1H), 8.21 (dd, J=7.9, 1.3 Hz, 1H), 7.62 (td, J=7.7, 1.4 Hz, 1H), 7.61 (td, J=7.7, 1.3 Hz, 1H), 7.51 (td, J=7.4, 1.3 Hz, 1H), 7.46 (td, J=7.5, 1.3 Hz, 1H), 7.19 (d, J=8.4 Hz, 1H), 7.15-7.11 (m, 2H), 7.08-7.04 (A$_1$A$_1$'B$_1$B$_1$', 2H), 7.05-6.96 (m, 5H), 6.95-6.91 (A$_1$A$_1$'B$_1$B$_1$', 2H), 6.91-6.81 (m, 3H), 5.90 (d, J=2.8 Hz, $^1$H), 3.84 (s, 3H), 3.52 (s, 3H), 2.31 (s, 3H), 2.29 (s, 3H), 2.16 (s, 3H), 1.26 (s, 3H) ppm.

$^{13}$C-NMR (CDCl$_3$, 101 MHz): δ=157.24, 157.22, 143.73, 143.68, 141.85, 141.55, 141.47, 140.96, 139.53, 139.32, 138.02, 137.41, 131.22, 130.96, 130.75, 130.49, 129.89, 129.78, 129.35 (2C), 129.32 (2C), 128.55, 128.42, 128.30, 127.74, 126.23 (2C), 126.20 (2C), 123.52, 123.46, 114.90, 114.79, 114.72, 114.60, 55.42, 54.81, 21.32, 21.29, 18.99, 18.25 ppm HRMS (ESI): calc. for C$_{21}$H$_{21}$O$_2$S$^+$ 337.1257; found 337.1251

EXAMPLE 3: ARYLATION WITH DOUBLE CONTROL OF AXIAL CHIRALITY

3.1 (1'S,2'R)-5-bromo-6'-methoxy-2,3'-dimethyl-2"-((S)-p-tolylsulfinyl)-1,1':2',1"-terphenyl

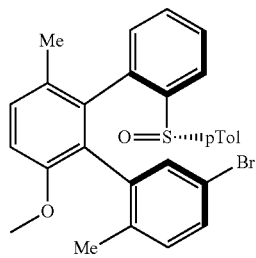

(1'S, 2'R)-5-bromo-6'-methoxy-2,3'-dimethyl-2"-((S)-(p-tolylsulfinyl)-1,1':2',1"-terphenyl
Chemical Formula: C$_{28}$H$_{25}$BrO$_2$S
Molecular Weight: 505,4700

Under air, in a an oven-dried pressure tube closed by a teflon screw cap were loaded (S)-5-methoxy-2-methyl-2'-(p-tolylsulfinyl)-1,1'-biphenyl (1 eq., 120 mg, 0.357 mmol), AgTFA (1 eq., 79 mg, 0.358 mmol), Ag$_2$CO$_3$ (2.5 eq., 246 mg, 0.892 mmol), 4 Å powdered molecular sieves (85 mg), Pd(TFA)$_2$ (25.3 mol %, 30 mg, 0.0902 mmol) and 1,3-bis(2,6-diisopropylphenyl)-1H-imidazol-3-ium chloride (50.1%, 76 mg, 0.179 mmol). HFIP (3400 µL) was then added and the resulting heterogeneous mixture was stirred at room temperature for 10 min. The reactor was then submerged in a 85° C. bath and stirred for 4 hours. After cooling down to room temperature the mixture was diluted with CH$_2$Cl$_2$, filtered on a silica gel pad (eluted with Et$_2$O) and the volatiles were removed under reduced pressure. Subsequent chromatography yielded (1'S,2'R)-5-bromo-6'-methoxy-2,3'-dimethyl-2"-((S)-p-tolylsulfinyl)-1,1':2',1"-terphenyl (92 mg, 0.182 mmol, 51%) as a yellow powder with a d.r. ≥98:2 (>95% conversion, crude d.r.=20.4: n.d. :1 overlapping signals).

$^1$H-NMR (CDCl$_3$, 400 MHz): δ=8.00 (dd, J=8.0, 1.1 Hz, 1H), 7.69 (d, J=2.1 Hz, 1H), 7.39 (td, J=7.7, 1.3 Hz, 1H), 7.26 (td, J=7.8, 1.4 Hz, 1H), 7.15 (td, J=8.3, 2.0 Hz, 1H), 7.15-7.04 (m, 5H), 6.98 (d, J=8.5 Hz, 1H), 6.96 (dd, J=7.5, 1.1 Hz, 1H), 6.82 (d, J=8.2 Hz, 1H), 3.76 (s, 3H), 2.33 (s, 3H), 1.84 (s, 3H), 1.14 (s, 3H) ppm.

$^{13}$C-NMR (CDCl$_3$, 101 MHz): δ=154.92, 143.28, 141.61, 141.14, 138.32, 136.95, 134.72, 132.78, 130.57, 130.11, 130.03, 129.79, 129.39 (2C), 129.37, 129.19, 128.34, 128.05, 126.45 (2C), 123.30, 118.54, 111.17, 55.78, 21.34, 19.44, 19.16 ppm. (1C overlapping not identified)

[α]$_D^{20}$=−6.4° (C=0.54, CHCl$_3$)

HRMS (ESI): calc. for C$_{28}$H$_{26}$BrO$_2$S$^+$ 505.0831; found 505.0822

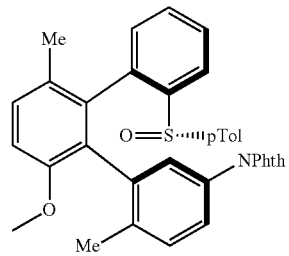

2-((1'S, 2'R)-6'-methoxy-3',6-dimethyl-2"-((S)-(p-tolylsulfinyl)-[1,1':2',1"-terphenyl]3-yl)isoindoline-1,3-dione
Chemical Formula: C$_{36}$H$_{29}$NO$_4$S
Molecular Weight: 571,6910

3.2. 2-(1'$_a$S,2'$_a$R)-6'-methoxy-3',6-dimethyl-2"-((S)-p-tolylsulfinyl)-[1,1':2',1"-terphenyl]-3-yl)isoindoline-1,3-dione An optimized procedure was conducted, giving a more synthetically useful yield, from (S)-5-dimethoxy-2-methyl-2'-(p-tolylsulfinyl)-1,1'-biphenyl (1 eq., 287 mg, 0.853 mmol), AgTFA (0.998 eq., 188 mg, 0.851 mmol), Ag$_2$CO$_3$ (2.34 eq., 551 mg, 2 mmol), 2-(4-iodo-3-methylphenyl)isoindoline-1,3-dione (1.28 eq., 396 mg, 1.09 mmol), 4 Å powdered molecular sieves (200 mg), Pd(TFA)$_2$ (30%, 85 mg, 0.256 mmol), 1,3-bis(2,6-diisopropylphenyl)-1H-imidazol-3-ium chloride (30.1%, 109 mg, 0.256 mmol) in hfip (9000 µL) for 5 hours. After cooling down to room temperature the mixture was diluted with CH$_2$Cl$_2$, filtered on a silica gel pad (eluted with Et$_2$O) and the volatiles were removed under reduced pressure. Subsequent chromatography yielded, affording 2-(1'S,2'R)-6'-methoxy-3',6-dimethyl-2"-((S)-p-tolylsulfinyl)-[1,1':2',1"-terphenyl]-3-yl) isoindoline-1,3-dione (358 mg, 0.626 mmol, 73%) as an off-white powder and with a d.r.≥98:2 (95% conversion, crude d.r.=n.d., overlapping signals).

$^1$H-NMR (CDCl$_3$, 400 MHz): δ=8.05 (dd, J=7.9, 1.3 Hz, 1H), 7.94-7.87 (m, 2H), 7.75-7.70 (m, 2H), 7.69 (d, J=2.2 Hz, 1H), 7.43 (td, J=7.7, 1.3 Hz, 1H), 7.28 (td, J=7.5, 1.3 Hz, 1H), 7.18 (dd, J=8.2, 2.3 Hz, 1H), 7.09 (d, J=8.3 Hz, 1H), 7.07-7.04 (m, 4H), 7.03 (d, J=15.7 Hz, 1H), 7.01 (dd, J=7.5, 1.2 Hz, 1H), 6.97 (d, J=4.3 Hz, 1H), 3.79 (s, 3H), 2.31 (s, 3H), 1.94 (s, 3H), 1.05 (s, 3H) ppm.

$^{13}$C-NMR (CDCl$_3$, 101 MHz): δ=167.17 (2C), 155.26, 143.16, 141.51, 141.31, 137.39, 137.03 (2C), 135.78, 133.92 (2C), 131.93, 130.05, 129.69, 129.67, 129.43 (2C), 129.27 (2C), 128.84, 128.66, 128.29, 127.87, 126.82 (2C), 125.45, 124.88, 123.55 (2C), 123.32, 111.43, 56.00, 21.37, 19.78, 19.09 ppm. [α]$_D^{20}$ =−5.54° (c=0.148, CHCl$_3$).

HRMS (ESI): calc. for C$_{36}$H$_{29}$NNaO$_4$S$^+$ 594.1701; found 594.1685

EXAMPLE 4: FUNCTIONAL GROUP INTERCONVERSION OF THE SULFINYL GROUP

4.1 ((1'R,2'S)-3'-methoxy-6',6''-dimethyl-[1,1':2',1''-terphenyl]-2,3''-diyl)bis(diphenylphosphane)

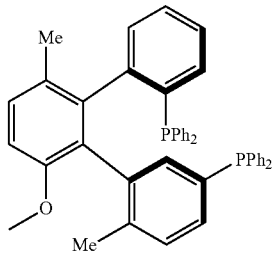

((1'R,2'S)-3'-methoxy-6',6''-dimethyl-[1,1':2',1''-terphenyl]2,3''-diyl)
bis(diphenylphosphane)
C$_{45}$H$_{58}$OP$_2$
656,7455

Anhydrous conditions: A solution of (1'S,2'R)-5-bromo-6'-methoxy-2,3'-dimethyl-2''-((S)-p-tolylsulfinyl)-1,1':2',1''-terphenyl (1 eq., 300 mg, 0.594 mmol) in Et$_2$O (6 mL) was cooled to −94° C. A solution of t-BuLi (5 eq., 1.55 M in pentane, 1.91 mL, 2.97 mmol) was then added dropwise (color changed to dark blue/maroon, some precipitate). The resulting mixture was stirred at −94° C. for 20 min., when a solution of ClPPh$_2$ (4.22 eq., 553 mg, 0.45 mL, 2.51 mmol) in toluene (0.5 mL) was slowly cannulated. The resulting mixture was allowed to reach −78° C. over 30 min., and was quenched by filtration over a silica gel pad under argon (washed with Et$_2$O, some DCM can be added to solubilize the reaction mixture). Solvent was removed under reduced pressure, and flash chromatography under argon (Et$_2$O/n-pentane 10:90, product loaded as 20:80 DCM/n-pentane solution) afforded ((1'R,2'S)-3'-methoxy-6',6''-dimethyl-[1,1':2',1''-terphenyl]-2,3''-diyl)bis(diphenylphosphane) (210 mg, 0.32 mmol, 54%) as a white powder. Recrystallization by layering a concentrated 80:20 CHCl$_3$/Et$_2$O solution with n-pentane afforded colorless crystals suitable for X-Ray analysis.

$^1$H-NMR (CDCl$_3$, 400 MHz): δ=7.69 (dd, J=10.7, 1.5 Hz, 1H), 7.36-6.94 (m, 29H), 6.92 (d, J=8.4 Hz, 1H), 6.80-6.73 (m, 1H), 3.72 (s, 3H), 2.03 (s, 3H), 1.25 (s, 3H) ppm.

$^{13}$C-NMR (CDCl$_3$, 101 MHz): δ=154.88, 146.42, 146.09, 140.97, 140.91, 138.42, 138.40, 138.37, 138.29, 138.25, 137.78, 137.71, 137.58, 137.28, 137.15, 137.12, 137.05, 136.75, 136.68, 136.52, 136.38, 135.22, 135.00, 133.85, 133.83, 133.80, 133.60, 133.21, 133.09, 133.06, 133.03, 132.91, 132.88, 131.92, 131.82, 131.56, 131.53, 129.65, 129.63, 129.54, 129.52, 129.20, 129.03, 128.97, 128.75, 128.47, 128.18, 128.16, 128.14, 128.11, 128.04, 128.00, 127.95, 127.79, 127.44, 126.79, 110.51, 55.83, 20.07, 19.41, 19.40 ppm.

$^{31}$P-NMR (CDCl$_3$, 162 MHz): δ=−6.94, −14.90 ppm.
[α]$_D^{20}$=+31.1 (c=1, CHCl$_3$)

HRMS (ESI): calc. for C$_{45}$H$_{39}$OP$_2$$^+$657.2471; found 657.2463

4.2. 1'R,2'S)-5''-chloro-3'-methoxy-2'',6'-dimethyl-[1,1':2',1''-terphenyl]-2-carboxylic acid

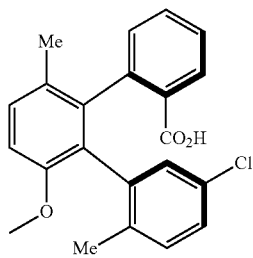

(1'R,2'S)-5''-chloro-3'-methoxy-2'',6'-dimethyl-[1,1':2',1''-terphenyl]-2-carboxylic acid
Chemical Formula: C$_{22}$H$_{19}$ClO$_3$
Molecular Weight: 366,8140

To a solution of (1S,1''R)-5-chloro-6'-methoxy-2,3'-dimethyl-2''-((S)-p-tolylsulfinyl)-1,1':2',1''-terphenyl (1 eq., 80 mg, 0.174 mmol) in THF (2000 μL) at −78° C. was added dropwise n-BuLi (4.15 eq., 1.6 M, 450 μL, 0.72 mmol). The mixture was stirred 3 min. at −78° C. (color changed from light yellow to darker orange), when gaseous CO$_2$ was bubbled into the reaction mixture, causing discoloration after few minutes. The resulting mixture was stirred at −78° C. for 30 min. with continuous CO$_2$ bubbling. It was quenched at −78° C. by addition of a MeOH solution in Et$_2$O, allowed back to room temperature, acidified to pH 1 by the addition of 1M HCl solution. The phases were separated and the organic phase was dried over Na$_2$SO$_4$. The volatiles were removed under reduced pressure and flash chromatography (CyH/EtOAc/AcOH 70:30:1) afforded (1'R,2'S)-5''-chloro-3'-methoxy-2'',6'-dimethyl-[1,1':2',1''-terphenyl]-2-carboxylic acid (47 mg, 0.128 mmol, 74%) as a yellowish solid with a d.r. >95:5 by $^1$H NMR, and a d.r. >99:1 by chiral HPLC.

Crystals suitable for X-ray analysis were grown in a round-bottom flask by layering a diluted DCM solution with n-pentane and letting the resulting mixture equilibrate at 4-6° C.

$^1$H-NMR (CDCl$_3$, 400 MHz): δ=10.96 (brd s, 1H), 7.93 (dd, J=7.8, 1.2 Hz, 1H), 7.30 (td, J=7.5, 1.4 Hz, 1H), 7.25-7.18 (m, 2H), 7.02-6.96 (m, 1H), 6.96-6.89 (m, 2H), 6.87 (d, J=8.2 Hz, 2H), 3.75 (s, 3H), 2.02 (s, 3H), 1.96 (s, 3H) ppm.

$^{13}$C-NMR (CDCl$_3$, 101 MHz): δ=171.49, 154.62, 141.97, 141.51, 139.06, 134.87, 132.19, 130.59, 130.48, 129.99, 129.95, 129.76, 129.47, 129.18, 127.68, 127.20, 126.93, 126.61, 109.37, 55.60, 19.87, 19.33 ppm.

[α]$_D^{20}$=−42.3° (c=0.230, CHCl$_3$).

HRMS (ESI): calc. for C$_{22}$H$_{19}$NaO$_3$$^+$389.0915; found 389.0892

EXAMPLE 5: SYNTHESIS OF MONOPHOSPHINE LIGAND

A selective functionalization of the triarylic bromo-sulfoxyde skeleton is realized by chemoselectif sulfoxide/Li exchange followed by the condensation with a methoxydiarylphosphine according to the following scheme

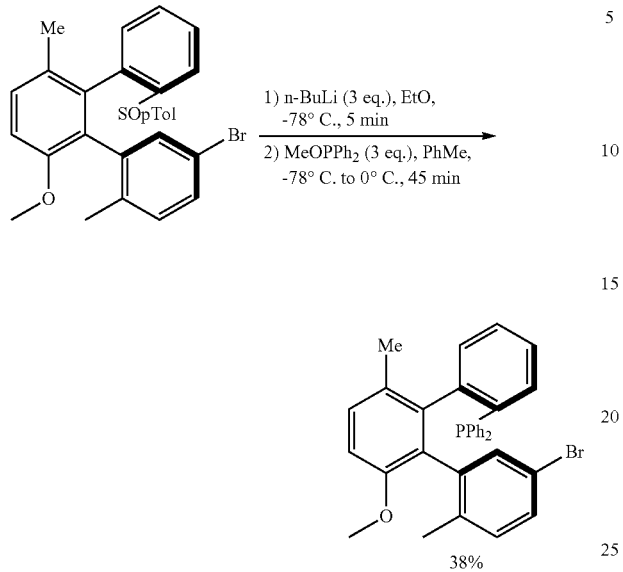

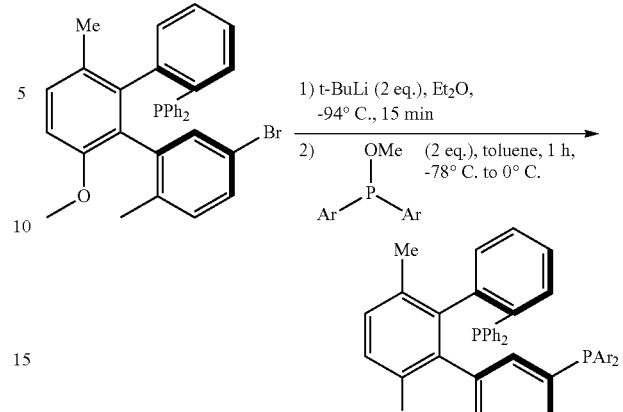

To a solution of 2-(5-bromo-2-methylphenyl)-1-methoxy-4-methyl-3-{2-[(S)-(4-methylphenyl)sulfinyl]phenyl}benzene (1 eq., 290 mg, 0.574 mmol) in toluene (5 mL) at −78° C., was added n-BuLi (3.35 eq., 1.6 M, 1.2 mL, 1.92 mmol) dropwise. The mixture was stirred 2 min when Et$_2$O (1 mL) cooled down to −78° C. was added and stirred 5 min at −78° C. A solution of ClPPh2 (3.4 eq., 430 mg, 0.35 mL, 1.95 mmol) in Et$_2$O (0.4 mL) was then added in one portion and stirred 15 min. at −78° C., then allowed to come back at 0° C. when the cooling bath was removed. The mixture was diluted with Et$_2$O and filtered under argon on silica plug. The solution was concentrated and purified by chromatography on silica gel push with argon (Et$_2$O/n-pentane 5:95, product loaded as 20:80 DCM/n-pentane solution) to afford ((1'R,2'S)-5''-bromo-3'-methoxy-2'',6'-dimethyl-[1,1':2',1''-terphenyl]-2-yl)diphenylphosphane (152 mg, 0.276 mmol, 48%) as a white powder.

$^1$H-NMR (500 MHz, Chloroform-d) δ: 7.67 (t, J=1.8 Hz, 1H), 7.48-7.10 (m, 15H), 7.07 (d, J=8.5 Hz, 1H), 7.00-6.91 (m, 2H), 3.74 (s, 3H), 2.00 (s, 3H), 1.26 (s, 3H) ppm $^{13}$C-NMR (126 MHz, CDCl$_3$) δ: 154.76, 146.40, 146.13, 141.10, 141.05, 140.00, 138.73, 138.64, 137.15, 137.06, 135.71, 135.37, 135.19, 134.11, 134.10, 132.96, 132.82, 132.24, 132.17, 130.67, 129.96, 129.63, 129.59, 129.57, 129.09, 128.82, 128.77, 128.53, 128.43, 128.36, 128.32, 127.65, 127.49, 127.20, 118.47, 110.40, 55.83, 19.73, 19.42 ppm $^{31}$P-NMR (202 MHz, CDCl$_3$) δ: −14.88 ppm $[α]_D^{20}$=+5.0° (c=1, CHCl$_3$)

EXAMPLE 6: SYNTHESIS OF DIPHOSPHINE LIGAND BEARING TWO DIFFERENT PHOSPHINE MOTIFS

The synthesis is realized according to the following scheme

EXAMPLE 6A

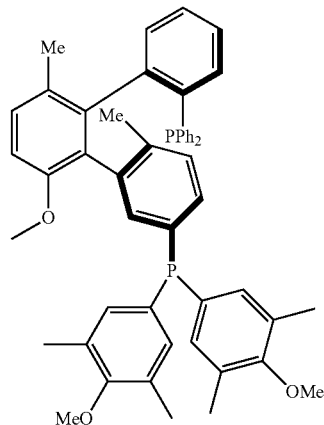

To a solution of {2-[2-(5-bromo-2-methylphenyl)-3-methoxy-6-methylphenyl]phenyl}diphenylphosphane (1 eq., 150 mg, 0.272 mmo) in anhydrous Et$_2$O (3.1 mL) cooled down to −94° C., t-BuLi (2.1 eq., 1.6 M, 0.357 mL, 0.571 mmol) is added dropwise and the reaction is stirred 20 min. A solution of methyl bis(4-methoxy-3,5-dimethylphenyl)phosphinite (2 eq., 180 mg, 0.544 mmol) in anhydrous toluene (0.25 mL) cooled down to −78° C. is then added and the reaction is stirred 1h and was allowed to warm to 0° C. Then the mixture is filtered over a silica plug under argon and then concentrated. Chromatography on silica gel (Et$_2$O/n-pentane 50:50, product loaded as 20:80 DCM/n-pentane solution) push with argon afforded {3-[2'-(diphenylphosphanyl)-3-methoxy-6-methyl-[1,1'-biphenyl]-2-yl]-4-methylphenyl}bis(4-methoxy-3,5-dimethylphenyl)phosphane (103 mg, 0.133 mmol, 49%) as a white solid.

$^1$H-NMR (400 MHz, Chloroform-d) δ: 7.61 (dd, J=10.2, 1.6 Hz, 1H), 7.20-7.15 (m, 4H), 7.13-6.86 (m, 12H), 6.81 (dd, J=8.2, 2.4 Hz, 3H), 6.75 (ddd, J=7.4, 5.2, 1.7 Hz, 1H), 6.69 (d, J=7.6 Hz, 2H), 3.62 (s, 3H), 3.61 (s, 3H), 3.59 (s, 3H), 2.09 (s, 6H), 2.07 (s, 6H), 1.94 (s, 3H), 1.09 (s, 3H) ppm $^{13}$C-NMR (126 MHz, CDCl$_3$) δ: 159.87, 157.92, 155.05, 155.02, 146.38, 146.11, 141.05, 141.00, 138.71, 138.61, 137.42, 137.31, 136.46, 136.39, 136.34, 136.22, 136.14, 135.82, 135.64, 135.58, 135.40, 134.58, 134.43, 134.28, 133.71, 133.28, 133.22, 133.14, 133.06, 132.98, 131.73, 130.91, 129.41, 129.07, 128.37, 128.31, 128.23, 128.20, 127.54, 127.03, 111.06, 110.87, 59.74, 59.69, 56.09, 20.34, 19.43, 16.25, 16.23 ppm $^{31}$P-NMR (162 MHz, CDCl$_3$) δ: −8.51, −15.18 ppm $[α]_D^{20}$ =+426.0° (c=0.32, CHCl$_3$)

EXAMPLE 6B

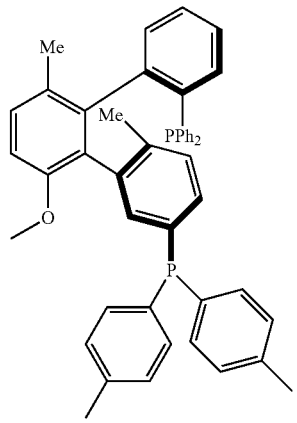

To a solution of {2-[2-(5-bromo-2-methylphenyl)-3-methoxy-6-methylphenyl]phenyl}diphenylphosphane (1 eq., 110 mg, 0.199 mmol) in anhydrous Et$_2$O (2.3 mL) cooled down to −94° C., t-BuLi (2.1 eq., 1.6 M, 0.262 mL, 0.419 mmol) is added dropwise and the reaction is stirred 20 min. A solution of methyl bis(4-methylphenyl)phosphinite (2 eq., 97.5 mg, 0.399 mmol) in anhydrous toluene (0.6 mL) cooled down to −78° C. is then added and the reaction is stirred 1h and was allowed to warm to 0° C. Then the mixture is filtered over a silica plug under argon and then concentrated. Chromatography on silica gel (Et$_2$O /n-pentane 10:90, product loaded as 20:80 DCM/n-pentane solution) push with argon afforded {3-[2'-(diphenylphosphanyl)-3-methoxy-6-methyl-[1,1'-biphenyl]-2-yl]-4-methylphenyl}bis(4-methylphenyl)phosphane (117 mg, 0.172 mmol, 86%) as a colorless oil.

$^1$H NMR (400 MHz, Chloroform-d) δ: 7.60 (dd, J=10.3, 1.6 Hz, 1H), 7.26-7.16 (m, 5H), 7.12-6.87 (m, 17H), 6.83 (dd, J=8.1, 6.7 Hz, 3H), 6.73 (ddd, J=7.5, 5.3, 1.8 Hz, 1H), 3.63 (s, 3H), 2.23 (s, 3H), 2.21 (s, 3H), 1.94 (s, 3H), 1.16 (s, 3H) ppm $^{31}$P-NMR (162 MHz, CDCl$_3$) δ: −8.44, −14.84 ppm $^{13}$C-NMR (101 MHz, CDCl$_3$) δ: 155.02, 146.50, 146.17, 141.08, 141.02, 138.48, 138.24, 137.86, 137.74, 137.59, 137.35, 137.22, 136.73, 136.62, 136.49, 136.49, 135.34, 135.11, 133.95, 133.91, 133.72, 133.40, 133.22, 133.17, 133.13, 132.99, 132.96, 131.58, 131.54, 129.29, 129.23, 129.17, 129.06, 128.99, 128.86, 128.28, 128.22, 128.11, 128.06, 127.52, 126.90, 110.65, 55.96, 21.35, 21.32, 20.20, 19.51 ppm $[α]_D$ =+15.6° (c=1.2, CHCl$_3$)

EXAMPLE 7: USE OF THE LIGANDS ACCORDING TO THE INVENTION

The ligand according to the invention may be used in asymmetric hydrogenation according to the following scheme

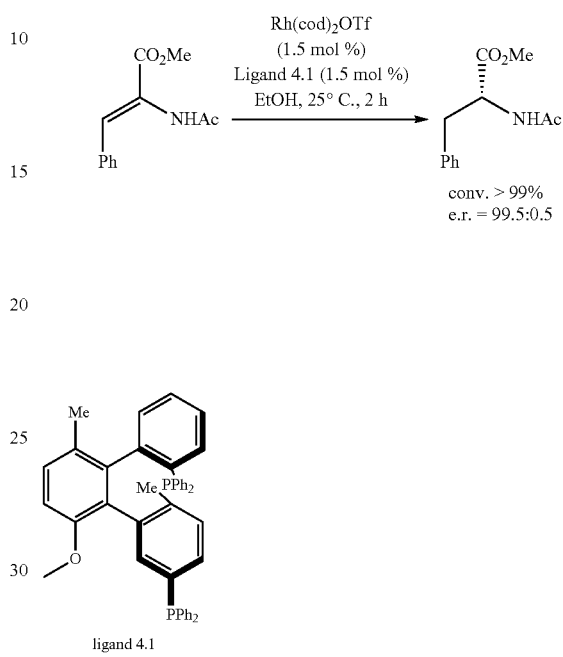

ligand 4.1

General Procedure:

In an oven-dried tube closed with a septum was loaded the substrate (1 equiv). Similarly an oven-dried schlenk closed with a septum was loaded with the metal (1.5-2 mol %) along with the ligand (2-2.5 mol %). Both vessels were evacuated under vacuum and back-filled with argon (4 times). Then the schlenk was put under vacuum, the stopcock closed and the vacuum was carefully broken with an hydrogen balloon. The required solvent was then added by mean of a syringe (~0.01 M) and the catalyst stock solution was stirred for 15 min in order to properly activate the complex. Meanwhile the required solvent was added to the substrate under argon, a hydrogen balloon fitted with a needle was inserted in the septum, vigorous stirring was started, and the required amount of the solution of the catalyst was added to the substrate (final concentration 0.1 M). The reaction was followed by $^1$H NMR and upon completion the solvent was removed under reduced pressure, the solid residue dissolved in DCM and filtrated over a silica gel plug to remove the catalyst (eluting with Et$_2$O or EtOAc) affording the pure, by $^1$H NMR, product with e.r. 99.5:0.5.

Analysis of the optical purity: Chiral HPLC conditions: ODH column, n-Hex/iPrOH 90:10, 0.5 mL/min, (tr$_1$: 19.8 min; tr$_2$: 25.8 min)

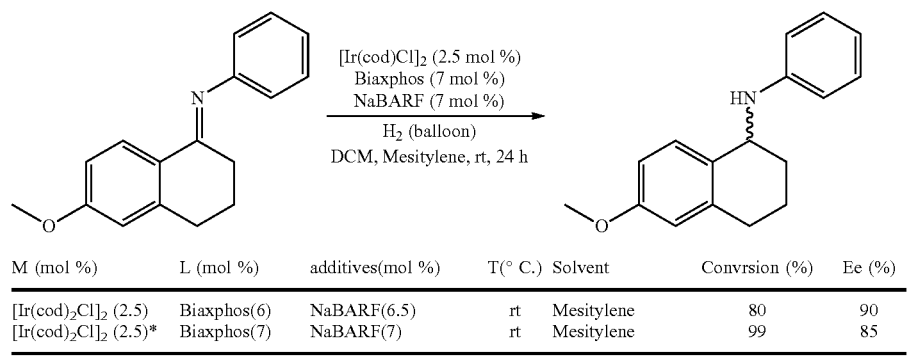

| M (mol %) | L (mol %) | additives(mol %) | T(° C.) | Solvent | Convrsion (%) | Ee (%) |
|---|---|---|---|---|---|---|
| [Ir(cod)$_2$Cl]$_2$ (2.5) | Biaxphos(6) | NaBARF(6.5) | rt | Mesitylene | 80 | 90 |
| [Ir(cod)$_2$Cl]$_2$ (2.5)* | Biaxphos(7) | NaBARF(7) | rt | Mesitylene | 99 | 85 |

*catalyst initially prepared in DCM

In the glove box, the bis(1,5-cyclooctadiene)diiridium(i) dichloride (2.55%, 2.73 mg, 0.00406 mmol), ligand 4.1 (7%, 7.32 mg, 0.0111 mmol) and NaBARF (7%, 9.87 mg, 0.0111 mmol) are placed in a schlenk. On the other hand, the (1E)-6-methoxy-N-phenyl-1,2,3,4-tetrahydronaphthalen-1-imine (1 eq., 40 mg, 0.159 mmol) is added to a tube. Both vessels were closed by a septum, removed from the glovebox and put under vacuum.

The vacuum in the schlenk was broken with an hydrogen balloon and the DCM (0.4 mL) was added. The solution was stirred for 30 min and then the solvent was removed under vacuum. Afterwards, the vacuum is broken with an hydrogen balloon and the mesitylene (0.4 mL) is added. The solution is stirred for 30 min. The mesitylene (1.1 mL) is added to the tube with the substrate under argon and finally the catalyst. The tube is put under hydrogen with a balloon and the reaction is stirred at room temperature for 24 h.

The reaction was followed by $^1$H NMR and upon completion the solution was filtrated over a celite plug (eluting with DCM) and concentrated to afford the 6-methoxy-N-phenyl-1,2,3,4-tetrahydronaphthalen-1-amine as a brown oil.

Enantiomeric ratio determination was carried out by HPLC on a chiral stationary phase against a racemic reference prepared by reduction of the same substrate NaBH$_4$ in EtOH.

Analysis of the optical purity: Daicel Chiracel ODH, n-Hex/i-PrOH 99:1, 0.5 mL/min. injection of 1 µL of 5 mg/mL solution in n-Hex/i-PrOH 80:20 (tr$_1$: 27.3 min; tr$_2$: 39.8 min).

$^1$H-NMR (400 MHz, Chloroform-d) δ: 7.31 (d, J=8.6 Hz, 1H), 7.20 (dd, J=8.6, 7.3 Hz, 2H), 6.82-6.60 (m, 5H), 4.59 (t, J=4.7 Hz, 1H), 3.80 (s, 3H), 2.99-2.54 (m, 2H), 2.16-1.71 (m, 4H) ppm.

The invention claimed is:

1. Enantiopure terphenyl presenting two ortho-located chiral axis having the following structural formula (I)

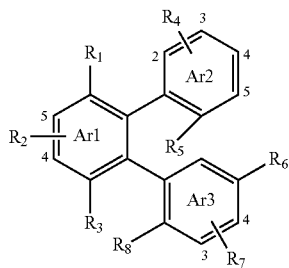

(I)

wherein
R$_1$ on the phenyl ring Ar1 represents
 a halogen atom, or
 a substituted or unsubstituted branched or straight alkyl group, or
 a substituted or unsubstituted cycloalkyl group, or
 a substituted or unsubstituted branched or straight alkoxy group, or
 a CH$_2$F group, or a CHF$_2$ group or a —CnF$_{n+2}$ group with n=1 to 10 or,
 a substituted or unsubstituted aryl group or,
 a —COR$_a$ or a —COOR$_a$ group with R$_a$ selected from a substituted or unsubstituted branched or straight alkyl group or a substituted or unsubstituted aryl group or
 a —NR$_b$R$_c$ group with R$_b$ and R$_c$ independently selected from a hydrogen atom, a substituted or unsubstituted branched or straight alkyl group or a substituted or unsubstituted aryl group or forming a NH$_2$-protecting group, or
 a BR$_a$R$_b$ group with R$_a$ and R$_b$, identical or different being as defined above or
 a —B(OR$_d$)(OR$_e$) group with R$_d$ and R$_e$ identical or different being selected from a hydrogen atom or a substituted or unsubstituted branched or straight alkyl group,
R$_2$ in position 4 or 5 of the phenyl ring Ar1 which bears it represents
 a hydrogen atom or
 a halogen atom,
 a substituted or unsubstituted branched or straight alkyl group or
 a substituted or unsubstituted cycloalkyl group, or
 a substituted or unsubstituted branched or straight alkoxy group or
 a substituted or unsubstituted aryl group or
 a —COR$_a$ or a —COOR$_a$ group with R$_a$ selected from a substituted or unsubstituted branched or straight alkyl group or a substituted or unsubstituted aryl group, or
 a —NR$_b$R$_c$ group with R$_b$ and R$_c$ independently selected from a hydrogen atom, a substituted or unsubstituted branched or straight alkyl group, or a substituted or unsubstituted aryl group, or forming a NH$_2$-protecting group or
 a —BR$_a$Rb group with R$_a$ and R$_b$ identical or different being as defined above or,
 a —B(OR$_d$)(OR$_e$) group with Rd and Re identical or different being selected from a hydrogen atom or a substituted or unsubstituted branched or straight alkyl group, $R_3$ on the phenyl ring Ar1 represents
a halogen atom or
a substituted or unsubstituted branched or straight alkyl group or,
a substituted or unsubstituted cycloalkyl group, or
a substituted or unsubstituted branched or straight alkoxy group or
a substituted or unsubstituted aryl group or
a —$COR_a$ or a —$COOR_a$ group with $R_a$ selected from
  a substituted or unsubstituted branched or straight alkyl group or a substituted or unsubstituted aryl group, or
a —$NR_bR_c$ group with $R_b$ and $R_c$ independently selected from a hydrogen atom, a substituted or unsubstituted branched or straight alkyl group, or a substituted or unsubstituted aryl group, or forming a $NH_2$-protecting group,
a —$BR_aR_b$ group with $R_a$ and $R_b$ identical or different being as defined above or,
a —$B(OR_d)(OR_e)$ group with $R_d$ and $R_e$ identical or different being selected from a hydrogen atom or a substituted or unsubstituted branched or straight alkyl group,
$R_4$, which may be in position 2, 3, 4 or 5 on the phenyl ring Ar1 which bears it, represents:
a hydrogen atom or
a halogen atom or
a substituted or unsubstituted branched or straight alkyl group or,
a substituted or unsubstituted cycloalkyl group, or
a $CH_2F$ group, or a $CHF_2$ group or —$CnF_{n+2}$ group with n=1 to 10, or
a substituted or unsubstituted aryl group, or
a —$OR_a$, a —$COR_a$ or a —$COOR_a$ group with $R_a$ selected from a substituted or unsubstituted branched or straight alkyl group or a substituted or unsubstituted aryl group, or
a —$NR_bR_c$ group with $R_b$ and $R_c$ independently selected from a hydrogen atom, a substituted or unsubstituted branched or straight alkyl group, or a substituted or unsubstituted aryl group, or forming a $NH_2$-protecting group, or
a —$BR_aR_b$ group with $R_a$ and $R_b$ identical or different being as defined above or,
a —$B(OR_d)(OR_e)$ group with $R_d$ and $R_e$ identical or different being selected from a hydrogen atom or a substituted or unsubstituted branched or straight alkyl group,
$R_5$ on the phenyl ring Ar1 represents a coordinating group or a substituent that will be used to install a coordinating group, selected from:
a halogen atom,
an —$OR_b$ group with Rb selected from a hydrogen atom, a substituted or unsubstituted branched or straight alkyl group, or a substituted or unsubstituted aryl group, or a $NH_2$-protecting group or
a —$CH_2OR_b$ group with $R_b$ selected from a hydrogen atom, a substituted or unsubstituted branched or straight alkyl group, or a substituted or unsubstituted aryl group, or
a —CHO group or
a —$COOR_b$ group with $R_b$ selected from a hydrogen atom, a substituted or unsubstituted branched or straight alkyl group, or a substituted or unsubstituted aryl group, or a $NH_2$-protecting group, or
a —$NR_bR_c$ group with $R_b$ and $R_c$ independently selected from a hydrogen atom, a substituted or unsubstituted branched or straight alkyl group, or a substituted or unsubstituted aryl group, or a $NH_2$-protecting group,
a —$SOR_a$ group or a —$SR_a$ group or a —$SO_2R_a$ with $R_a$ selected from a substituted or unsubstituted branched or straight alkyl group or a substituted or unsubstituted aryl group, or
a —$PR_aR_d$ or a —$P(O)R_an_d$ with $R_a$ and $R_d$ independently selected from a substituted or unsubstituted branched or straight alkyl group or a substituted or unsubstituted aryl group, or
a —$C=NR_b$ with $R_b$ as defined above or
a substituted or unsubstituted oxazoline group or
a substituted or unsubstituted indenyl group or
a substituted or unsubstituted cyclopentadienyl group,
$R_6$ on the phenyl ring Ar3 is a coordinating group
either represents
a hydrogen atom or
a halogen atom,
an —OH group
a substituted or unsubstituted branched or straight alkyl group or
a substituted or unsubstituted cycloalkyl group, or
a substituted or unsubstituted aryl group or
a —$SOR_a$ group or a —$SR_a$ group or a —$SO_2R_a$ with $R_a$ selected from a substituted or unsubstituted branched or straight alkyl group or a substituted or unsubstituted aryl group, or
a —$OR_a$, a —$COR_a$ or a —$COOR_a$ group with $R_a$ selected from a substituted or unsubstituted branched or straight alkyl group or a substituted or unsubstituted aryl group, or
a —$NR_bR_c$ group with $R_b$ and $R_c$ independently selected from a hydrogen atom, a substituted or unsubstituted branched or straight alkyl group, or a substituted or unsubstituted aryl group, or forming a $NH_2$-protecting group or,
a —$BR_aR_b$ group with $R_a$ and $R_b$ identical or different being as defined above or,
a —$B(OR_d)(OR_e)$ group with $R_d$ and $R_e$ identical or different being selected from a hydrogen atom or a substituted or unsubstituted branched or straight alkyl group,
a —$PR_aR_d$ or a —$P(O)R_aR_d$ with $R_a$ and $R_d$ independently selected from a substituted or unsubstituted branched or straight alkyl group or a substituted or unsubstituted aryl group, or
a substituted or unsubstituted or oxazoline group
a substituted or unsubstituted indenyl group or
a substituted or unsubstituted cyclopentadienyl group,
or may form with $R_5$
a bridged phosphoric acid or ester or phosphinate represented by formula

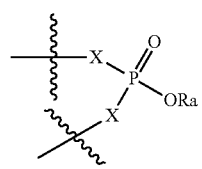

with X being a carbon or an oxygen atom and Ra selected from a hydrogen atom or a substituted or unsubstituted branched or straight alkyl group; or a bridged phosphoramidite or phosphoramine represented by formula

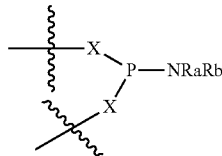

with X being a carbon or an oxygen atom and Ra and Rb selected from a substituted or unsubstituted branched or straight alkyl group or a substituted or unsubstituted aryl group, $R_7$ which may be in position 3 or 4 on the phenyl ring Ar3 which bears it represents:
a hydrogen atom or
a halogen atom or
a substituted or unsubstituted branched or straight alkyl group or,
a substituted or unsubstituted branched or straight alkoxy group
a substituted or unsubstituted cycloalkyl group, or
a $CH_2F$ group, or a $CHF_2$ group or $-CnF_{n+2}$ group with n=1 to 10, or
a substituted or unsubstituted aryl group, or
a $-OR_a$, a $-COR_a$ or a $-COOR_a$ group with $R_a$ selected from a substituted or unsubstituted branched or straight alkyl group or a substituted or unsubstituted aryl group, or
a $-NR_bR_c$ group with $R_b$ and $R_c$ independently selected from a hydrogen atom, a substituted or unsubstituted branched or straight alkyl group, or a substituted or unsubstituted aryl group, or forming a $NH_2$-protecting group, or
a $-BR_aR_b$ group with $R_a$ and $R_b$ identical or different being as defined above or,
a $-B(OR_d)(OR_e)$ group with $R_d$ and $R_e$ identical or different being selected from a hydrogen atom or a substituted or unsubstituted branched or straight alkyl group, $R_8$ on the phenyl ring Ar3 represents
a halogen atom or
a substituted or unsubstituted branched or straight alkyl group, or a substituted or unsubstituted branched or straight alkoxy group or
a $-OR_a$ group with $R_a$ selected from a substituted or unsubstituted branched or straight alkyl group or a substituted or unsubstituted aryl group, or
a substituted or unsubstituted aryl group or
a $-COR_a$ or a $-COOR_a$ group with $R_a$ selected from a substituted or unsubstituted branched or straight alkyl group or a substituted or unsubstituted aryl group, or
a $-NR_bR_c$ group with $R_b$ and $R_c$ independently selected from a hydrogen atom, a substituted or unsubstituted branched or straight alkyl group, or a substituted or unsubstituted aryl group, or a forming $NH_2$-protecting group, or
a $-BR_aR_b$ group with $R_a$ and $R_b$ identical or different being as defined above or,
a $-B(OR_d)(OR_e)$ group with $R_d$ and $R_e$ identical or different being selected from a hydrogen atom or a substituted or unsubstituted branched or straight alkyl group.

2. The enantiopure terphenyl according to claim 1, wherein
$R_1$ represents
a halogen atom,
a substituted or unsubstituted branched or straight alkyl group, or
a substituted or unsubstituted branched or straight alkoxy group, or
a $CF_3$ group,
$R_2$ represents
a hydrogen atom, or
a substituted or unsubstituted branched or straight alkyl group, or
a substituted or unsubstituted branched or straight alkoxy group,
$R_3$ represents
a substituted or unsubstituted branched or straight alkyl group, or
a substituted or unsubstituted branched or straight alkoxy group,
$R_4$ represents
a hydrogen atom, or
a halogen atom, or
a substituted or unsubstituted branched or straight alkoxy group, or
a substituted or unsubstituted branched or straight alkyl group, or
an aryl group, or
a $CH_2F$ group, or a $CHF_2$ group or $-CnF_{n+2}$ group with n=1 to 10,
$R_5$ represents
a $SOR_a$ group with $R_a$ selected from a substituted or unsubstituted branched or straight-$(C_1$-$C_4)$ alkyl group, or a substituted or unsubstituted aryl group, or
a OH group, or
$PR_aR_d$ or a $-P(O)R_aR_d$ with $R_a$ and $R_d$ independently selected from a substituted or unsubstituted branched or straight alkyl group and a substituted or unsubstituted aryl group,
$R_6$ represents
a hydrogen atom,
a halogen atom, or
a substituted or unsubstituted branched or straight-$(C_1$-$C_4)$ alkyl group, or
a substituted or unsubstituted branched or straight-$(C_1$-$C_4)$ alkoxy group, or
$PR_aR_d$ or a $-P(O)$Rand with $R_a$ and $R_d$ independently selected from a substituted or unsubstituted branched or straight alkyl group and a substituted or unsubstituted aryl group, or
a $-NR_bR_c$ group with $R_b$ and $R_c$ independently selected from a hydrogen atom, a substituted or unsubstituted branched or straight alkyl group, and a substituted or unsubstituted aryl group, or a $NH_2$-protecting group,
$R_7$ represents
a hydrogen atom,
a substituted or unsubstituted branched or straight-$(C_1$-$C_4)$ alkyl group, or
a substituted or unsubstituted branched or straight-$(C_1$-$C_4)$ alkoxy group, or
a $CF_3$ group,
$R_8$ represents
a hydrogen atom,
a halogen atom,
a substituted or unsubstituted branched or straight-$(C_1$-$C_4)$ alkyl group, or a substituted or unsubstituted branched or straight-$(C_1-C_4)$ alkoxy group, or
a $CF_3$ group.

3. Process for preparing the compounds of formula (I) according to claim 1, said process comprising the step of:
reacting an enantiopure compound of formula (1)

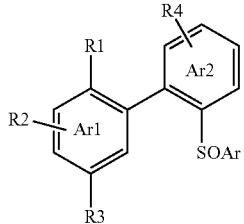

wherein $R_1$, $R_2$, $R_3$ and $R_4$ are as defined in claim 1 and Ar is selected from substituted or unsubstituted aryl groups,
with a compound of formula (2)

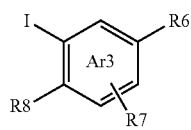

with $R_6$, $R_7$ and $R_8$ as defined in claim 1,
in presence of a silver salt comprising a mixture of $Ag_2CO_3$ and AgTFA, a N-heterocyclic carbene precursor, a palladium catalyst and a molecular sieve of 3 Å to 5 Å in a solvent selected from the flurorinated alcools and the fluorinated ethers at a temperature comprised between 40 and 120° C. during 2 to 24 hours to obtain a compound of formula (Ia)

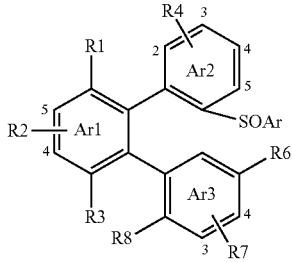

wherein $R_1$, $R_2$, $R_3$, $R_4$, $R_6$, $R_7$ and $R_8$ are as defined in claim 1 and Ar is selected from substituted or unsubstituted aryl groups,
replacing or substituting the —SOAr group in order to obtain a compound of formula (I)

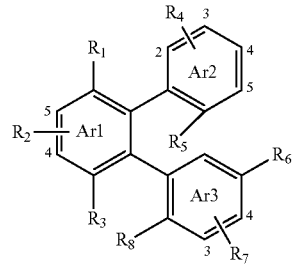

wherein $R_1$, $R_2$, $R_3$, $R_4$, $R_6$, $R_7$ and $R_8$ are as defined in claim 1 and $R_5$ is as defined in claim 1 and is not —SOAr.

4. A method for performing asymmetric organometallic reactions, comprising providing the compound of formula (I) of claim 1, and applying the compound (I) as a mono or bidentate ligand.

5. Enantiopure compounds of formula (1)

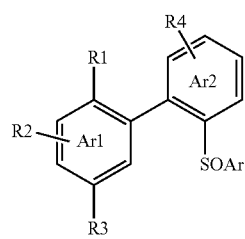

wherein $R_1$, $R_2$ and $R_4$ are as defined in claim 1, $R_3$ is as defined in claim 1 but is not a hydrogen and Ar is selected from substituted or unsubstituted aryl groups.

6. The process of claim 3, wherein the molecular sieve is of 4 Å.

7. The process of claim 3, wherein the reacting step is performed at a temperature between 75 and 85° C.

8. The process of claim 6, wherein the reacting step is performed at a temperature between 75 and 85° C.

9. The process of claim 3, wherein the reacting step is performed for 2 to 10 hours.

10. The process of claim 6, wherein the reacting step is performed for 2 to 10 hours.

11. The process of claim 7, wherein the reacting step is performed for 2 to 10 hours.

12. The process of claim 8, wherein the reacting step is performed for 2 to 10 hours.

13. A method for performing asymmetric catalysis, comprising providing the compound (I) of claim 1, and applying the compound of formula (I) as organocatalyst, as chiral base and as generator, with metal, of isolable chiral metallic complexes.

14. A method for performing asymmetric hydrogenation comprising providing the compound (I) of claim 1, and applying the compound of formula (I) as organocatalyst.

* * * * *